United States Patent [19]

Atwell et al.

[11] Patent Number: 5,732,115
[45] Date of Patent: Mar. 24, 1998

[54] ENHANCEMENT OF MEASUREMENT ACCURACY IN BULK MATERIAL ANALYZER

[75] Inventors: Thomas L. Atwell, La Jolla; Raymond J. Proctor; Chaur-Ming Shyu, both of San Diego; Chris A. Isaacson, Poway; Andrew H. Smith, Escondido, all of Calif.

[73] Assignee: Gamma-Metrics, San Diego, Calif.

[21] Appl. No.: 492,575

[22] Filed: Jun. 20, 1995

Related U.S. Application Data

[63] Continuation of Ser. No. 89,274, Jul. 9, 1993, abandoned.
[51] Int. Cl.$^6$ .................................................. G21G 1/06
[52] U.S. Cl. ................................................ 376/159
[58] Field of Search .......................... 376/159, 157, 376/153–155; 250/393.01–390.07, 390.11, 391, 392, 336.1, 357.1, 370.09, 491.1; 209/589; 266/168

[56] References Cited

U.S. PATENT DOCUMENTS

| | | | |
|---|---|---|---|
| 3,053,388 | 9/1962 | Tittle | 376/159 |
| 3,124,679 | 3/1964 | Tittman et al. | 376/159 |
| 3,146,349 | 8/1964 | Jordan | 376/159 |
| 3,278,747 | 10/1966 | Ohmart | 250/83.3 |

(List continued on next page.)

FOREIGN PATENT DOCUMENTS

| | | | |
|---|---|---|---|
| 747312 | 5/1970 | Belgium | 376/257 |
| 2066233 | 1/1992 | Canada . | |

OTHER PUBLICATIONS

Strahlenther, Onkol., vol. 165, (1989), pp. 87–90, Less et al.
Nuclear Instruments and Methods, vol. 75, (1969), pp. 13–33, Krinninger et al.
LA-6788-PR, (Jun. 1977), Sapir, pp. 1–54.

*Primary Examiner*—Harvey E. Behrend
*Attorney, Agent, or Firm*—Edward W. Callan

[57] ABSTRACT

In a bulk material analyzer in which bulk material is received in an activation region between a pair of neutron sources laterally disposed on one side of the activation region for emitting neutrons for bombarding the bulk material within the activation region to cause gamma-rays to be emitted from the bombarded bulk material and a pair of gamma-ray detectors laterally disposed on another side of the activation region for detecting gamma-rays emitted from the bulk material, a primary neutron moderator is disposed about the neutron sources for reducing the velocity of the emitted neutrons; and a secondary neutron moderator is disposed about the primary neutron moderator for further reducing the velocity of the neutrons and is further disposed adjacent the lateral edges of the activation region for channeling and reflecting the neutrons into the activation region. The two gamma-ray detectors are disposed toward opposite lateral edges of the activation region, with each detector being skewed so that a portion of each detector that is closer to the edge of the activation region toward which the detector is disposed than to the lateral center of the activation region is disposed closer to a plane passing laterally through the center of the activation region than is another portion of each detector that is closer to the lateral center of the activation region than to the edge of the activation region toward which the detector is disposed. Spatial compensators are disposed adjacent the same side of the activation region as the detectors for reflecting neutrons toward the activation region at a greater density toward opposite lateral edges of the activation region than toward the center of the activation region. Bladders containing a liquid primary neutron moderating material that expands and contracts with temperature variations, such as heavy water, are tightly packed within a compartment for maintaining a substantial quantity of the liquid material between the neutron sources and the activation region notwithstanding thermal contraction of the liquid material; and a resilient compressible foam is disposed about the bladders for enabling the tight packing of the liquid material to be maintained notwithstanding expansion and contraction of the liquid material.

9 Claims, 2 Drawing Sheets

U.S. PATENT DOCUMENTS

| | | | |
|---|---|---|---|
| 3,631,247 | 12/1971 | Barton, Jr. | 250/83.3 R |
| 3,794,843 | 2/1974 | Chen | 250/392 |
| 3,881,110 | 4/1975 | Hounsfield et al. | 250/360 |
| 3,889,112 | 6/1975 | Holmes et al. | 376/159 |
| 4,028,267 | 6/1977 | Christell et al. | 250/359 |
| 4,041,315 | 8/1977 | Hounsfield | 250/360 |
| 4,314,155 | 2/1982 | Sowerby | 250/390 |
| 4,582,992 | 4/1986 | Atwell et al. | 376/159 |
| 4,672,648 | 6/1987 | Mattson et al. | 378/4 |
| 4,682,043 | 7/1987 | Marshall | 376/159 |
| 4,809,172 | 2/1989 | Hopkinson et al. | 378/901 |
| 5,076,502 | 12/1991 | Kitaguchi et al. | 209/589 |
| 5,098,640 | 3/1992 | Gozani et al. | 376/159 |
| 5,124,554 | 6/1992 | Fowler et al. | 376/159 |
| 5,144,140 | 9/1992 | Allyson et al. | 376/159 |
| 5,153,439 | 10/1992 | Gozani et al. | 376/159 |
| 5,162,095 | 11/1992 | Alegre et al. | 376/159 |
| 5,162,096 | 11/1992 | Gozani | 376/159 |

ENHANCEMENT OF MEASUREMENT ACCURACY IN BULK MATERIAL ANALYZER

This is a continuation of application Ser. No. 08/089,274 filed on Jul. 9, 1993, now abandoned.

BACKGROUND OF THE INVENTION

The present invention generally pertains to bulk material analyzers and is particularly directed to improving the spatial uniformity of gamma-ray detection in bulk material analyzers of the type in which the bulk material is bombarded by neutrons within an activation region.

Bulk material analyzers are used to measure the elemental content of bulk materials. One type of bulk material analyzer includes one or more neutron sources and one or more gamma-ray detectors. When the bulk material within an activation region between at least one neutron source disposed on one side of the activation region and at least one gamma-ray detector disposed on another side of the activation region opposite from said one side is bombarded by neutrons, secondary emissions of gamma-rays are produced from the bulk material and detected by the gamma-ray detector(s). The gamma-ray detector(s) produce signals which are processed to provide an indication of the elemental content of the bulk material. Different characteristic gamma-ray energy spectra are produced from different elements in the bulk material. By processing detected signals that are indicative of the gamma-ray spectrum, a measurement is provided of the quantitative elemental content of the bulk material. This measurement process is known in the art as prompt gamma-ray neutron activation analysis (PGNAA).

In prior art bulk material analyzers, the response of the gamma-ray detectors to gamma-ray emission from different areas of a cross-sectional profile of the activation region is extremely non-uniform, with said response being less for a given quantity of a given bulk material located near the edges of the activation region than for the same given quantity of the same given bulk material located at the center of the activation region. Therefore, the measured quantity of a given element within a non-homogeneous bulk material is dependent upon the particular location of such given element in a cross-sectional profile of the activation region.

SUMMARY OF THE INVENTION

The present invention provides a bulk material analyzer in which measurement accuracy is enhanced by improving the spatial uniformity of response by the gamma-ray detector(s) to gamma-ray emission from different areas of a cross-sectional profile of the activation region.

The present invention provides a bulk material analyzer in which bulk material is received in an activation region between at least one neutron source and at least one gamma-ray detector, comprising a conveyor belt having upwardly and outwardly extended sides, a container having surfaces defining said activation region, wherein the container surfaces further define a passageway for enabling bulk material to be transported through said activation region on the conveyor belt; at least one neutron source disposed within the container beneath the passageway on one side of the activation region for emitting neutrons for bombarding bulk material being transported on the conveyor belt through said activation region to cause gamma-rays to be emitted from said bombarded bulk material; at least one gamma-ray detector disposed within the container above the passageway on another side of the activation region opposite from said one side for detecting gamma-rays emitted from said bombarded bulk material; a primary neutron moderator disposed about said neutron source(s) for reducing the velocity of said emitted neutrons; and a secondary neutron moderator disposed about the primary neutron moderator for further reducing the velocity of said neutrons and further disposed adjacent said one side of the activation region at which the neutron source(s) are disposed, for channeling and reflecting said neutrons into said activation region, wherein a lower portion of the passageway-defining surfaces define a trough having upwardly and outwardly extended sides adjacent said activation region for cradling the conveyor belt; and wherein the secondary neutron moderator is further disposed adjacent the sides of the trough for channeling and reflecting said neutrons into said activation region.

The spatial uniformity of response of the detectors to gamma-ray emission from different areas of various cross-sectional profiles of the activation region is further improved by providing at least two neutron sources and/or at least two gamma-ray detectors. Preferably, there are two neutron sources, which are separated laterally from the center of said one side of the activation region, and two said gamma-ray detectors, which are disposed toward opposite ends of said other opposite side of the activation region, with each detector being skewed so that a portion of each detector that is closer to the end of said other opposite side toward which said detector is disposed than to the center of said other opposite side is disposed closer said one side of said activation region than is another portion of each detector that is closer to said center of said other opposite side than to said end of said other opposite side toward which said detector is disposed.

The spatial uniformity of response of the detectors to gamma-ray emission from different areas of various cross-sectional profiles of the activation region is still further improved by providing spatial compensating means disposed adjacent said other opposite side of the activation region for reflecting neutrons toward said activation region at a greater density toward opposite ends of said other opposite side than toward the center of said other opposite side; and including neutron moderating material respectively disposed over the detectors for reflecting neutrons toward said activation region in accordance with proximity to the center of said other opposite side of said activation region, with said reflection increasing in a direction away from the center of said other opposite side.

The spatial uniformity of response of the detectors to gamma-ray emission from different areas of a cross-sectional profile of the activation region is also improved by providing a tertiary neutron moderator disposed about the secondary neutron moderator for further reducing the velocity of said neutrons and for reflecting said neutrons into the secondary neutron moderator, and for isolating the secondary neutron moderator from the radiation shielding material. The tertiary neutron moderator is also disposed adjacent radiation shielding material within the container for isolating the secondary neutron moderator from the radiation shielding material.

Additional features of the present invention are described in relation to the detailed description of the preferred embodiments.

DETAILED DESCRIPTION

Figure 1:
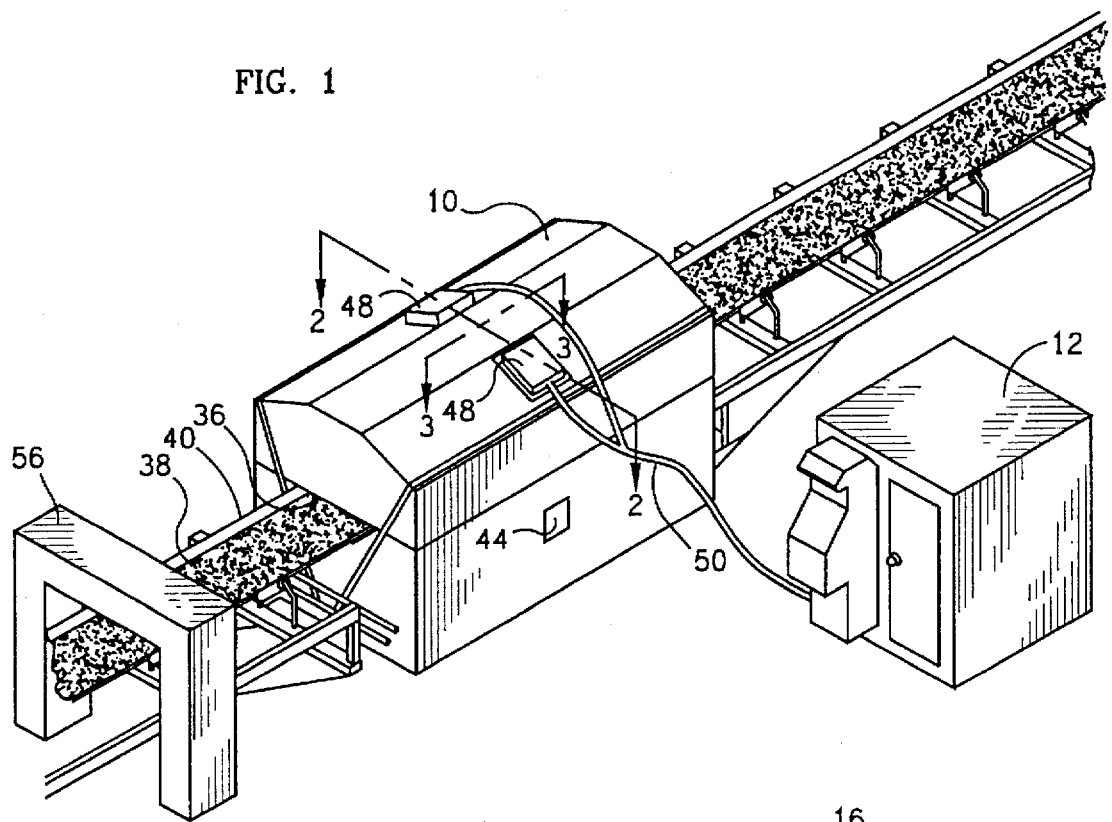
FIG. 1 is a perspective view illustrating a preferred embodiment the bulk material analyzer of the present invention with a conveyor belt transporting bulk material through the material analyzer assembly.
Figure 2:
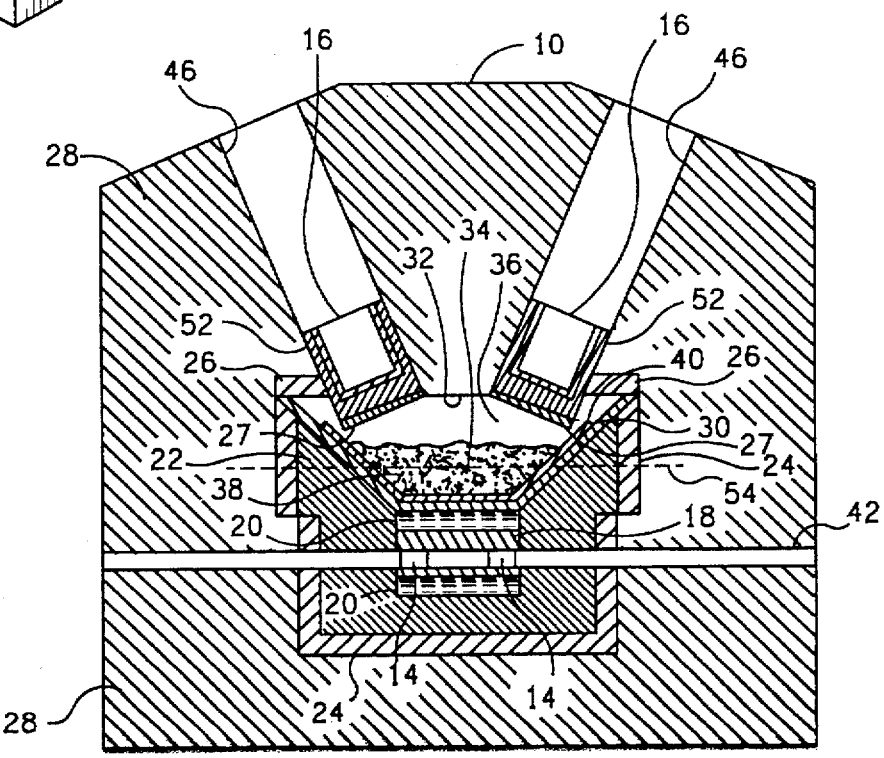
FIG. 2 is a sectional elevation view taken along lines 2—2 showing the construction of the bulk material analyzer adjacent the activation region.
Figure 3:
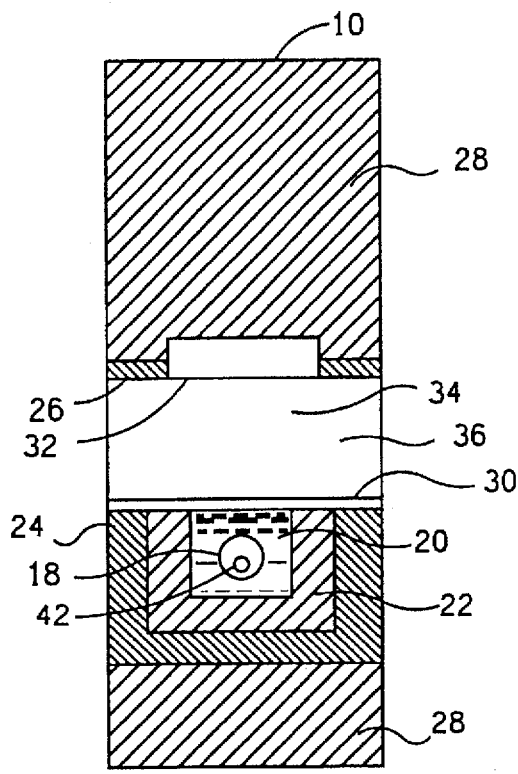
FIG. 3 is a sectional elevation view taken along lines 3—3 further showing the construction of the bulk material analyzer adjacent the activation region.

Referring to FIGS. 1, 2 and 3, a preferred embodiment of a bulk material analyzer according to the present invention includes a container 10, a data processor (not shown) within a separate housing 12, a pair of neutron sources 14, a pair of gamma-ray detectors 16, a gamma-ray shield 18, a primary neutron moderator 20, a secondary neutron moderator 22, a tertiary neutron moderator 24, spatial compensators 26, 27 and radiation shielding material 28.

The container 10 has interior surfaces 30, 32 defining an activation region 34 between the neutron sources 14 and the gamma-ray detectors 16. A lower portion 30 of the passageway-defining surfaces 30, 32 defines a trough 30 having upwardly extended sides adjacent the activation region 34. The container surfaces 30, 32 further define a passageway 36 for enabling bulk material 38 to be transported through the activation region 34 on a conveyor belt 40.

The neutron sources 14 are disposed within the container 10 beneath the passageway 36 on one side of the activation region 34 for emitting neutrons for bombarding bulk material 38 being transported on a conveyor belt 40 through the activation region 34 to cause gamma-rays to be emitted from the bombarded bulk material 38. The neutron sources 14 are inserted through a tubular neutron source cavity 42 in the container 10 into selected positions beneath the passageway 36, and are separated laterally on opposite sides of the longitudinal axis of the passageway 36. The neutron sources 16 are inserted into the neutron source cavity 42 through a door 44 in the container 10. Lateral separation of the neutron sources 14 suppresses the response of the gamma-ray detectors 16 to a given quantity of a given bulk material 38 located at the center of the activation region 34.

The gamma-ray detectors 16 are disposed within the container 10 above the passageway 36 on another side of the activation region 34 opposite from the one side for detecting gamma-rays emitted from the bombarded bulk material 38. The gamma-ray detectors 16 are inserted through detector cavities 46 in the container 10 into selected positions above the passageway 36. The gamma-ray detectors 16 are inserted into the detector cavities 46 through hatches 48 in the container 10. Signals produced by the gamma-ray detectors 16 are provided by electrical cables 50 to the data processor within the housing 12.

The gamma-ray shield 18 is a heavy metal, which is disposed within the container 10 about the neutron sources 14 for shielding the detectors 16 from gamma rays emitted from the neutron sources 14 so as to minimize detection by the detectors 16 of gamma rays from other than the bulk material 38 in the activation region 34.

A neutron shield 52 is disposed about each gamma-ray detector 16 for the detectors 16 from stray neutrons so as to prevent detection by the detectors 16 of gamma rays secondarily emitted from within the gamma-ray detectors 16 as result of bombardment by neutrons of materials within the gamma-ray detectors 16.

The primary neutron moderator 20 is disposed about the neutron sources 14 for reducing the velocity of the neutrons emitted from the neutron sources 14. Reduction of neutron velocity enhances capture of the neutrons by the bulk material 38 so as to produce gamma-ray emission from the bulk material 38.

The secondary neutron moderator 22 is disposed about the primary neutron moderator 20 for further reducing the velocity of neutrons emitted from the neutron sources 14. The secondary moderator 22 is further disposed adjacent the sides of the trough 30 for channeling and reflecting the slower neutrons into the activation region 34 to thereby enhance the response of the gamma-ray detectors 16 for a given quantity of a given bulk material 38 located near the edges of the activation region 34.

The portion of the trough 30 adjacent the primary moderator 20 and the secondary neutron moderator 22 is made of a neutron transmissive material that enables the neutrons to diffuse into the activation region 34 from the primary moderator 20 and the secondary neutron moderator 22.

The tertiary neutron moderator 24 is disposed about the secondary neutron moderator 22 and adjacent the radiation shielding material 28 for further reducing the velocity of the neutrons, for reflecting the neutrons into the secondary neutron moderator 22, and for isolating the secondary neutron moderator 22 from the radiation shielding material 28, which would absorb the neutrons, rather than reflect the neutrons.

The two gamma-ray detectors 16 are disposed toward opposite ends of the other opposite side of the activation region 34, with each detector 16 being skewed so that a portion of each detector 16 that is closer to the end of the other opposite side toward which the detector 16 is disposed than to the center of the other opposite side is disposed closer to a plane 54 parallel to the other opposite side and passing through the center of the activation region 34 than is another portion of each detector 16 that is closer to the center of the other opposite side than to the end of the other opposite side toward which said detector 16 is disposed. Such skewing of the gamma-ray detectors 16 further enhances the response of the gamma-ray detectors 16 for a given quantity of a given bulk material 38 located near the edges of the activation region 34, and also suppresses the response of the gamma-ray detectors 16 to said given quantity of said given bulk material 38 located at the center of the activation region 34.

Still additional enhancement of the response of the gamma-ray detectors 16 for a given quantity of a given bulk material 38 located near the edges of the activation region 34, and suppression of the response of the gamma-ray detectors 16 to said given quantity of said given bulk material 38 located at the center of the activation region 34 is provided by the spatial compensators 26, which are disposed near the edges of the activation region 34 and the spatial compensators 27, which are disposed over the ends of the gamma-ray detectors 16 that are adjacent the activation region 34.

In one embodiment, in which the spatial compensators 26, 27 are primarily neutron moderating material, the spatial compensators 26, 27 are disposed adjacent said other opposite side of the activation region 34 for reflecting neutrons toward the activation region 34 at a greater density toward opposite ends of the other opposite side than toward the center of the other opposite side. The spatial compensators 27 are wedges of neutron moderating material having a thickness that increases in a direction away from the center of the other opposite side of the activation region 34, as shown in FIG. 2.

In an alternative embodiment, the spatial compensators 27 are respectively disposed over the gamma-ray detectors 16 for gradually attenuating gamma-ray detection by the detectors 16 in accordance with proximity to the center of the other opposite side of the activation region 34, with said attenuation increasing in a direction toward the center of said other opposite side. The spatial compensators 27 are wedges of gamma-ray absorbing material having a thickness that decreases in a direction away from the center of the other opposite side of the activation region 34, which is the opposite from that which is shown in FIG. 2 for the neutron-reflecting material wedges.

The number of neutron sources 14 and the number of gamma-ray detectors 16 is dependent upon the width of the activation region 34, and may be increased beyond two neutron sources 14 and two gamma-ray detectors 16 as required to optimize the spatial uniformity of response by the gamma-ray detectors 16. The equivalence of two or more neutron sources 14 and/or two or more gamma-ray detectors 16 can be provided by rapid reciprocal movement of one neutron source 14 and/or one gamma-ray detector 16, respectively, between two or more locations.

The spatial uniformity of response of the gamma-ray detectors 16 to gamma-ray emission from different areas of a cross-sectional profile of the activation region 34 is also dependent upon the cross-sectional profile of the bulk material 38 on the conveyor belt 40 within the activation region 34, as defined by the depth of the bulk material 38 at different lateral positions of a cross-section normal to the direction of movement of the conveyor belt 40, as shown in FIG. 2. Accordingly, the disposition of the neutron sources 14 within the neutron source cavity 42 and the disposition of the gamma-ray detectors 16 within detector cavities 46 may be adjusted in accordance with the cross-sectional profile of the bulk material 38 on the belt 40 within the activation region 34.

In one embodiment, a profile of the bulk material 38 within the activation region 34 is determined continuously as the bulk material 38 is being transported by the conveyor belt 40 through the activation region 34; and the disposition of the neutron sources 14 and/or the disposition of the gamma-ray detectors 16 are dynamically adjusted in accordance with said determined profile. Said profile is determined by the data processor in the housing 12 in response to signals provided by a sensing apparatus 56 disposed in advance of the activation region 34 in the direction of movement of the conveyor belt 40; and the data processor controls positioning apparatus (not shown) within the container 12 to dynamically adjust the disposition of the neutron sources 14 and/or the disposition of the gamma-ray detectors 16 in accordance with said determined profile so that when the bulk material 38 having the profile determined at the position of the sensing apparatus 56 reaches the activation region 34, the neutron sources 14 and/or the gamma-ray detectors 16 are so disposed as to optimize the spatial uniformity of the response of the gamma-ray detectors 16. The sensing apparatus 56 may include any commonly known distance and direction sensing means such as radar, sonar, or laser beam range finding equipment.

Figure 4:
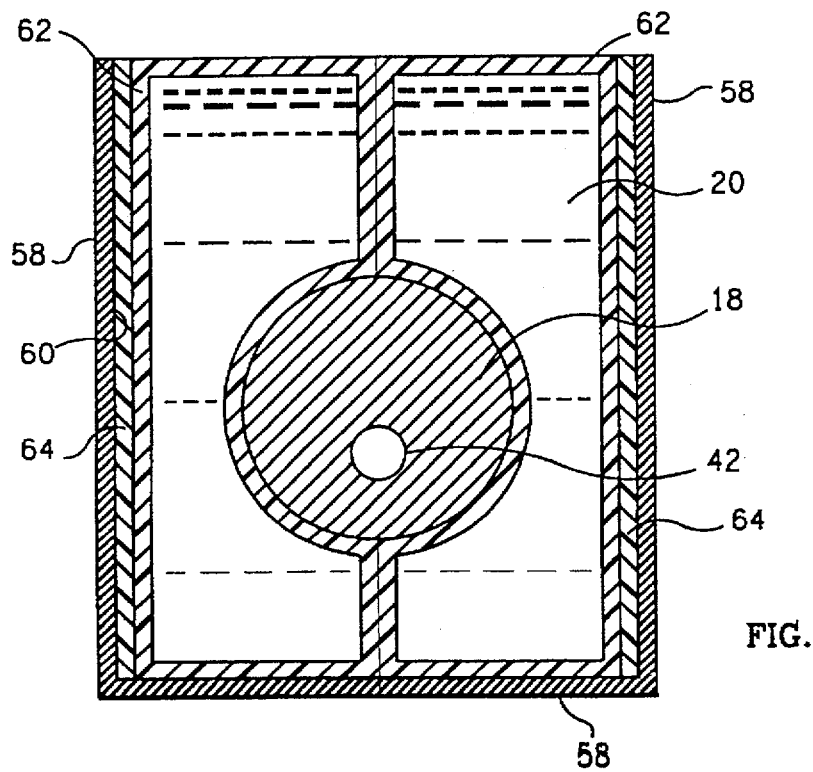
FIG. 4 is an enlarged sectional elevation view taken in the same plane as FIG. 3 showing the portion of the bulk material analyzer that includes the primary neutron moderator.

In one preferred embodiment, the primary neutron moderator 20 includes a liquid material, such as heavy water $D_2O$, that expands and contracts with variations in temperature. In this embodiment, the container 10 includes a set of side and bottom walls 58 of secondary neutron moderating material defining a compartment 60 for containing the liquid primary moderator material 20, as shown in FIG. 4. A pair of bladders 62 containing the liquid material 20 are disposed by being tightly packed within the compartment 60 for maintaining a substantial quantity of the liquid primary moderator material 20 between the neutron sources 14 and the activation region 34 notwithstanding thermal contraction of the liquid primary moderator material 20. The bladders 62 are contoured to fit tightly around the gamma-ray shield 18. A resilient compressible material 64, such as a closed cell foam is disposed about the bladders 62 for enabling such tight packing of the liquid primary moderator material 20 to be maintained notwithstanding expansion and contraction of the liquid material 20.

We claim:

1. A bulk material analyzer in which bulk material is received in an activation region between at least one neutron source and at least one gamma-ray detector, comprising a conveyor belt having upwardly and outwardly extended sides;

a container having surfaces defining said activation region, wherein the container surfaces further define a passageway for enabling bulk material to be transported through said activation region on the conveyor belt;

at least one neutron source disposed within the container beneath the passageway on one side of the activation region for emitting neutrons for bombarding bulk material being transported on the conveyor belt through said activation region to cause gamma-rays to be emitted from said bombarded bulk material;

at least one gamma-ray detector disposed within the container above the passageway on another side of the activation region opposite from said one side for detecting gamma-rays emitted from said bombarded bulk material;

a primary neutron moderator disposed about said neutron source(s) for reducing the velocity of said emitted neutrons; and a secondary neutron moderator disposed about the primary neutron moderator for further reducing the velocity of said neutrons and further disposed adjacent said one side of the activation region at which the neutron source(s) are disposed, for channeling and reflecting said neutrons into said activation region;

wherein a lower portion of the passageway-defining surfaces define a trough having upwardly and outwardly extended sides adjacent said activation region for cradling the conveyor belt; and wherein the secondary neutron moderator is further disposed adjacent the sides of the trough for channeling and reflecting said neutrons into said activation region.

2. A bulk material analyzer according to claim 1, wherein two said gamma-ray detectors are disposed toward opposite ends of said other opposite side of the activation region, with each detector being skewed so that a portion of each detector that is closer to the end of said other opposite side toward which said detector is disposed than to the center of said other opposite side is disposed closer to said one side of said activation region than is another portion of each detector that is closer to said center of said other opposite side than to said end of said other opposite side toward which said detector is disposed.

3. A bulk material analyzer according to claim 2, further comprising
   a pair of spatial compensators including neutron moderating material respectively disposed over the detectors for reflecting neutrons toward said activation region in accordance with proximity to the center of said other opposite side of said activation region, with said reflection increasing in a direction away from the center of said other opposite side.

4. A bulk material analyzer according to claim 3, wherein there are two said neutron sources, which are separated laterally on opposite sides of the longitudinal axis of the passageway.

5. A bulk material analyzer according to claim 1, further comprising
   spatial compensating means disposed adjacent said other opposite side of the activation region for reflecting neutrons toward said activation region at a greater density toward opposite ends of said other opposite side than toward the center of said other opposite side.

6. A bulk material analyzer according to claim 1, wherein there are at least two said so disposed neutron sources and at least two said so disposed gamma-ray detectors.

7. A bulk material analyzer according to claim 1, further comprising
   radiation shielding material disposed within the container; and
   a tertiary neutron moderator disposed about the secondary neutron moderator and adjacent the radiation shielding material for further reducing the velocity of said neutrons, for reflecting said neutrons into the secondary neutron moderator, and for isolating the secondary neutron moderator from the radiation shielding material.

8. A bulk material analyzer according to claim 1, wherein there are two said neutron sources, which are separated laterally on opposite sides of the longitudinal axis of the passageway.

9. A bulk material analyzer according to claim 1, wherein a portion of the trough adjacent the primary neutron moderator and the secondary neutron moderator is made of a neutron transmissive material that enables said neutrons to diffuse into said activation region from the primary neutron moderator and the secondary neutron moderator.

* * * * *